United States Patent [19]

Yoshida et al.

[11] Patent Number: 4,496,585
[45] Date of Patent: Jan. 29, 1985

[54] POWDERED OR GRANULAR SOLID PESTICIDE COMPOSITION

[75] Inventors: Mamoru Yoshida, Odawara; Hidejiro Yokoo, Tokyo; Ei Shirai, Omiya, all of Japan

[73] Assignee: Showa Denko Kabushiki Kaisha, Tokyo, Japan

[21] Appl. No.: 515,832

[22] Filed: Jul. 21, 1983

[30] Foreign Application Priority Data

Jul. 21, 1982 [JP] Japan ................... 57-125872

[51] Int. Cl.$^3$ ............... A01N 47/46; A01N 47/48
[52] U.S. Cl. ................... 514/514; 514/770
[58] Field of Search ........................... 424/302

[56] References Cited

U.S. PATENT DOCUMENTS

| | | | |
|---|---|---|---|
| 3,113,908 | 12/1963 | Pieroh et al. | 424/358 |
| 4,010,431 | 8/1978 | Oita | 424/364 |
| 4,115,130 | 9/1978 | Crump et al. | 424/288 |

Primary Examiner—Leonard Schenkman
Assistant Examiner—Joseph A. Lipovsky
Attorney, Agent, or Firm—Sughrue, Mion, Zinn, Macpeak and Seas

[57] ABSTRACT

A powdered or granular solid pesticide composition comprising methyl isothiocyanate supported on natural or synthetic faujasite type zeolite particles having an effective micro-pore diameter of 3.5 to 6 angstrom. This pesticide composition can effectively control various plant parasitic nematodes and noxious soil organisms and can remarkably facilitate application work.

4 Claims, No Drawings

POWDERED OR GRANULAR SOLID PESTICIDE COMPOSITION

BACKGROUND OF THE INVENTION

1. Field of the Invention

The present invention relates to a powdered or granular solid pesticide composition. More specifically, it relates to a powdered or granular solid pesticide composition, containing methyl isothiocyanate ("MITC" hereinbelow) as an effective component, capable of effectively controlling various plant parasitic nematodes and noxious soil fungi and insects which inhibit normal growth of plants by parasitic action in subterranean roots and tubers of plants in soil and capable of being readily applied to soil as a nematocide, a fungicide, and an insectcide with excellent applicability.

2. Description of the Prior Art

MITC represented by the chemical formula $CH_3NCS$ is very volatile low melting point solid having a vapor pressure of 20.7 mmHg at 20° C., a melting point of 35° C., and a boiling point of 119° C. It is commercially available as a nematocide, fungicide, and a said insecticide in the form of an oily preparation dissolved in an organic solvent. However, these MITC preparations have problems in that their application is troublesome since they must be injected into the soil at predetermined injection points through a special applicator and that the concentration distribution of the MITC is caused around each injection point and, therefore, uniform and effective pesticidal effects cannot be obtained and cultivated crops are susceptible to phytotoxity (or chemical damages).

Various attempts have been made to solve the above-mentioned problems. For example, powdered or granular pesticide compositions in which active components are supported on solid carriers have been conventionally used as a one preparation form of pesticide compositions for soil application. These solid type pesticide compositions have the advantage, as compared with the liquid type pesticide compositions, that uniform pesticide effects can be obtained and phytotoxity due to high local concentration of pesticides in soil does not easily occur since the solid type pesticide compositions can be readily and simply applied to soil and can also be readily mixed into soil without a special application therefor. However, the preparation of powdered or granular MITC compositions is difficult in practice for the following reasons:

(1) Since MITC is extremely volatile as mentioned above, it is very difficult to retain MITC stably on a solid carrier;

(2) Even if MITC can be supported on a solid carrier to some extent, the supported MITC tends to volatilize at once when a container containing the supported MITC is opened;

(3) Since the vapor of MITC is lachrymatory and skin irritative, volatilization of MITC during application is very noxious to an operator or worker; and (4) When MITC is completely and densely solidified with a carrier, the above-mentioned volatilization and vaporization problems can be solved.

However, too dense solidification causes too slow releasing of MITC from the solidified MITC agents, which, in turn, causes phytotoxity due to the retention of MITC in soil for a long term and causes insufficient pesticide effects due to the too small releasing of MITC. Furthermore, the use of too expensive substances and complex preparation steps is not practical for pesticide compositions from an economical viewpoint.

SUMMARY OF THE INVENTION

The object of the present invention is to provide a powdered or granular solid pesticide composition capable of stably retaining a relatively large amount of MITC and also capable of moderately releasing the MITC after mixing with soil to be treated, desirably releasing substantially all MITC within about one day, without causing volatilization of MITC during storage and spreading.

Another object of the present invention is to provide a powdered or granular solid pesticide composition having appropriate fluidity, economy, and practicability, Other objects and advantages of the present invention will be apparent from the following description.

In accordance with the present invention, there is provided a powdered or granular solid pesticide composition comprising methyl isothiocyanate supported on natural or synthetic faujasite type zeolite particles having an effective micro-pore diameter of 3.5 to 6 angstroms.

DESCRIPTION OF THE PREFERRED EMBODIMENTS

The present inventors have found that natural or synthetic faujasite type zeolite particles can unexpectedly adsorb and retain a relatively large amount of MITC with good adsorbability and stability and can desirably release the adsorbed MITC after mixing with soil to be treated. Thus, the above-mentioned objects of the present invention can be attained by the use of natural or synthetic faujasite type zeolite particles, whereas other carrier substances conventionally used in the production of pesticide compositions cannot attain the above-mentioned objects of the present invention.

Chemically speaking, zeolites are hydrated alkali metal or alkaline earth metal salts of crystalline aluminosilicates having a three-dimensional pore structure. Various kinds of natural or synthetic zeolites are known. Of these zeolites, only faujasite type zeolite particles having an effective micro-pore diameter of about 3.5 to 6 angstroms can be used to attain the above-mentioned objects of the present invention. Zeolites especially desirable in the present invention are type A synthetic zeolites having the chemical formula:

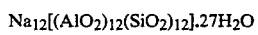

$$Na_{12}[(AlO_2)_{12}(SiO_2)_{12}]\cdot 27H_2O$$

or those in which substitutable sodium cations of the above formula are partially substituted with calcium cations. These zeolite particles are effectively used in the preparation of the present solid pesticide compositions after activating the same by dehydration.

The particle size of the natural or synthetic faujasite type zeolite usable as a carrier in the present invention is not especially limited. For example, a powdered zeolite having a particle size of 300 mesh or less to a granular zeolite having a particle size of about 10 to 50 mesh or a molded zeolite having a particle size of about several millimeters or other various shapes can be used in the present invention. The zeolite is desirably used after granulating the same into appropriate sizes by an extrusion granulating method, a rotary granulating method, a compression granulating method, or other conventional granulating methods. In the practice of the granulation of the zeolite, bentonite, clay, talc, kaolin, calcium carbonate, diatomaceous earth, and similar substances can be optionally used as a binder, lubricant, or bulk filler from the viewpoints of improvements in the mechanical strength and flowability (or fluidity) of the zeolite particles or a decrease in the production cost.

It should be noted that the zeolite be sufficiently dehydrated by a thermal treatment before MITC is supported thereon. This is because, since the zeolite possibly contains water, the stable adsorbability of MITC cannot be obtained. Although thermal treatment conditions are not specifically limited, the zeolite may be generally subjected to a thermal treatment at a temperature of 100° C. to 700° C., desirably 200° C. to 500° C. for about 1 to 10 hours.

The amounts of MITC supported on the zeolite are not specifically limited. However, a too small amount of MITC supported on the zeolite particles naturally necessitates a large amount of powdered or granular solid pesticide compositions in the application thereof. Contrary to this, a too large amount of MITC supported on the zeolite particles results in instability in the adsorption amount of MITC. Accordingly, MITC is desirably supported on the zeolite generally in an amount of 0.05 to 0.5 parts by weight, desirably 0.08 to 0.2 parts by weight, based on 1 part by weight of the zeolite.

MITC can be supported on the zeolite particles by any conventional method such as a dipping method. Generally, MITC is supported on the zeolite particles by contacting MITC in the form of liquid with the zeolite carrier particles to effect the adsorption of MITC into the zeolite particles. Since MITC has a melting point of about 35° C. and is in a solid state at an ambient temperature, MITC is generally melted by heating or is generally dissolved in a suitable solvent. The solvent usable for dissolving MITC in the production of the present pesticide composition are not specifically limited as long as MITC does not react with or decompose in the solvent. Desirable solvents are aprotic solvents which are compatible with MITC. Typical examples of such solvents are aromatic hydrocarbons such as benzene, toluene, and xylene; linear or cyclic aliphatic hydrocarbons such as pentane, hexane, heptane, octane, and cyclohexane; halogenated hydrocarbons such as dibromoethane dichloropropane, dichloropropene, chlorobenzene, and dichlorobenzene; and cyclic aliphatic ether such as tetrahydrofuran and dioxane.

Furthermore, biologically active compounds against noxious organisms in soil such as the other nematocides, fungicides, and insecticides, in addition to MITC, can be optionally supported on the zeolite particles. Especially when the above-mentioned biologically active compounds are in a liquid state at an ambient temperature and are compatible with MITC, these compounds can also conveniently serve as the above-mentioned solvents.

The powdered or granular solid pesticide composition of the present invention containing, as an effective component, MITC and, optionally other active compounds can be applied in the same manner as in conventional pesticides for soil treatment. The amount of the pesticide composition to be applied to plants is substantially the same as in the conventional pesticides containing MITC and, optionally, other active components for soil fungi, soil insects and weeds.

The powdered or granular solid pesticide composition of the present invention can be effectively applied to soil as preplant treatment for controlling various nematodes living as a parasite in subterranean roots and tubers of plants and living as a parasite in terrestrial stems, leaves, and flowers invading from the soil into plant bodies. Examples of these nematodes are tylenchidae such as potato rot nematode, bulb and stem nematode; anguindae such as bentgrass nematode; pratylenchidae such as tobacco stunt nematode and sugarcane stylet nematode; pratylenchidae such as rice root nematode, coffee root-lesion nematode, California root-lesion nematode, Cobb root-lesion nematode, Scribner root-lesion nematode, corn root-lesion nematode, walnut root-lesion nematode and root-lesion nematode; hoplolamidae such as spiral nematode and Cobb spiral nematode; heteroderidae such as potato cyst nematode, oat cyst nematode, cactus cyst nematode, upland rice cyst nematode, soybean cyst nematode, hop cyst nematode, clover cyst nematode and cystoid nematode; meloidogynidae such as peanut root-knot nematode, northern root-knot nematode, southern root-knot nematode, Javanese root-knot nematode, apple root-knot nematode and Thames root-knot nematode; tylenchulidae such as citrus nematode; paratylenchidae such as ramie pin nematode and South African pin nematode; aphelenchoididae such as rice white-tip nematode, strawberry nematode and chrysanthemum foliar nematode; longidoridae such as needle nematode and American dagger nematode; trichodoridae such as stubby root rematode.

The application amounts of the powdered or granular solid pesticide compositions of the present invention may be varied over a wide range depending upon, for example, varieties of plants to be applied, kinds of nematodes to be controlled, extent of damages, soil conditions, seasons, and weather conditions. Generally speaking, the powdered or granular solid pesticide compositions are applied in an amount of 1 to 5 kg, desirably 2 to 3 kg for nematodes and soil insects and 3 to 4 kg for fungi, in terms of the amount of the effective component, per 1 are of the field.

The powdered on granular solid pesticide compositions can be applied to fields as follows. For example, an adequate amount of the compositions is simply applied on the surface of rows by any conventional means and, then, is incorporated into soil with a hoe, tiller, or tractor. Thereafter, the soil is allowed to stand for desirably about a few or several days.

EXAMPLE

The present invention now will be further illustrated by, but is by no means limited to, the following examples, in which all percentages and parts are expressed on a weight basis unless otherwise specified.

EXAMPLE 1

A 2 part amount of MITC was dissolved in 1 part of xylene and, then, 12 parts of each carrier listed below was added thereto to be allowed to stand for one day in a sealed vessel. Thus, MITC was supported on the carrier. A 2 g amount of the supported carrier was sampled. The sample was placed in a glass schale having diameter of 95 mm and was allowed to stand in a room at a temperature of 24° C. and a relative humidity of 70%. At predetermined time intervals, the supported powdered or granular composition samples were taken and, then, were subjected to extraction as follows. That is, 2 g of the sample was extracted by shaking with 20 ml of acetone containing 10% of water and the acetone extract was gas chromatographically analyzed by using cyclohexanone as an internal standard substance. The extraction was carried out at a room temperature by shaking for one hour, allowing the sample to stand for one night, and again shaking for one hour.

The results are shown in Table 1.

List of Carriers used in Example 1

A: White carbon prepared by adding 30% of bentonite to white carbon and, then, extrusion granulating the same into granules having a diameter of 1.6 mm, followed by drying at 100° C. for 1 hour.

B: Diatomaceous earth prepared in the same manner as mentioned in sample A.

C: Sintered diatomaceous earth prepared in the same manner as mentioned in sample A.

D: Commercially available granular activated carbon having an average particle size of 0.5 mm.

E: Commercially available granular vermiculite having a particle size of 1 to 2 mm.

F: Commercially available granular sintered kaoline having a particle size of 0.4 to 1 mm G: Commercially available granular Japanese acid clay (Montmorillonite having a particle size of 0.7 to 1.9 mm.

H: Commercially available granular activated Japanese acid clay having a particle size of 0.9 to 1.9 mm.

I: Commercially available natural mordenite type zeolite having a particle size of 1.0 to 2.0 mm (manufactured by Nitto Funka Industries Co., Ltd.)

J: Natural mordenite type zeolite (manufactured by Kunimine Industries Co., Ltd.) prepared in the same manner as described in sample A.

K: Commercially available synthetic faujasite type zeolite having a particle diameter of 1.6 mm and an effective pore diameter of about 2.5 Å (Molecular sieve 3A manufacture by Union Carbide Corporation (UCC))

L: Commercially available synthetic faujasite type zeolite having a particle diameter of 1.6 mm and an effective pore diameter of about 3.4 Å (Molecular sieve 4A manufactured by UCC)

M: Commercially available synthetic faujasite type zeolite having a particle diameter of 1.6 mm and an effective pore diameter of about 4.2 Å (Molecular sieve 5A manufactured by UCC)

N: Commercially available synthetic faujasite type zeolite having a particle diameter of 1.6 mm and an effective pore diameter of about 9 Å (Molecular sieve 10X manufactured by UCC)

O: Commercially available synthetic faujasite type zeolite having a particle diameter of 1.6 mm and an effective pore diameter of about 10 Å (Molecular sieve 13X manufactured by UCC)

P: Commercially available synthetic faujasite type zeolite having a particle diameter of 1.6 mm and an effective pore diameter of about 9 Å (Molecular sieve SK-40 manufactured by UCC)

Q: Commercially available synthetic mordenite type zeolite having a particle diameter of 1.6 mm and an effective pore diameter of about 4 Å (Molecular sieve AW-300 manufactured by UCC)

R: Commercially available natural chabazite/Erionite type Zeolite having a partide diamter of 1.6 mm and an effective pore diameter of about 4.3 Å (Molecular sieve Zeolon 500 manufactured by Norton Chemical Process Products)

S: Commercially available natural clinoptiolite type zeolite having a particle diameter of 1.6 mm and an effective pore diameter of about 3.5 Å (Molecular sieve Zeolon 400 manufactured by Norton Chemical process Products)

T: Commercially available synthetic mordenite type zeolite having a particle diameter of 1.6 mm and an effective pore diameter of about 8-9 Å (Molecular sieve Zeolon 900H manufactured by Norton Chemical Process Products)

TABLE 1

| Granular Composition | MITC retention amount (%) Lapse of time (min) after preparation | | | |
| --- | --- | --- | --- | --- |
|  | 0 | 30 | 60 | 120 |
| A | 12.7 | 2.0 | 0 | 0 |
| B | 12.2 | 1.1 | 0 | 0 |
| C | 12.5 | 1.2 | 0 | 0 |
| D | 12.3 | 1.8 | 0 | 0 |
| E | 12.4 | 1.0 | 0 | 0 |
| F | 12.6 | 1.0 | 0 | 0 |
| G | 12.5 | 2.7 | 1.1 | 0 |
| H | 12.4 | 3.4 | 1.0 | 0 |
| I | 12.6 | 3.3 | 2.7 | 1.8 |
| J | 12.5 | 3.5 | 2.8 | 2.4 |
| K | 12.5 | 1.3 | 0.9 | 0 |
| L | 12.5 | 9.4 | 7.3 | 5.8 |
| M | 12.4 | 12.0 | 11.5 | 10.7 |
| N | 12.5 | 4.7 | 2.3 | 0.4 |
| O | 12.7 | 2.9 | 1.4 | 0 |
| P | 12.6 | 5.2 | 2.9 | 0.6 |
| Q | 12.7 | 3.8 | 1.2 | 0 |
| R | 12.7 | 5.6 | 2.5 | 0.7 |
| S | 12.6 | 1.7 | 0.5 | 0 |
| T | 12.6 | 1.8 | 1.6 | 1.1 |

As is clear from the results shown in Table 1, the supported MITC was rapidly volatilized to decrease the remaining amount in the carrier at an open state in a short time of period in samples A to K and N to T, whereas the supported MITC was retained in samples L and M. Furthermore, as shown in samples K to P, the MITC retention capability of the carriers largely depend upon the effective pore diameter in the same faujasite type zeolites.

EXAMPLE 2

Field soil infested by southern root-knot nematodes was packed at a depth of 20 cm in a 1/5000 are Wagner pot. The pesticide composition samples B, F, K, L, M, and O prepared in Example 1 were spread over the surface of the soil in an amount of 4 kg MITC/10 ares of soil. After being allowed to stand for designated period listed in Table 2, the samples were sufficiently mixed with the soil in the pots and were covered by poly(vinylchloride) sheet. The pots were allowed to stand for one week under ambient conditions.

After one week, the soil in the pots was thoroughly mixed and allowed to stand for one day and, then, two young seedlings of cucumber were planted and grown. After 3 weeks, the roots were taken out from the soil and the number of root knots formed were counted. The numbers of the root knots were standardized as a classification value according to the following:

| Classification value | Parasitic degree of root-knots nematode |
| --- | --- |
| 0 | None |
| 1 | Very slight |
| 2 | Slight |

-continued

| Classification value | Parasitic degree of root-knots nematode |
| --- | --- |
| 3 | Moderate |
| 4 | Heavy |

The root-knot index and the root-knot nematode controlling rate were determined by the following equations:

Root-knot index =

$$\frac{\Sigma(\text{Classification value} \times \text{Number of plant classified therein})}{\text{Total test plant number} \times 4} \times 100$$

Root-knot nematode protective value =

$$100 - \frac{\text{Root-knot index of Test pot}}{\text{Root-knot index of Control pot}} \times 100$$

The tests were carried out three times in each test sample and the average data was used for calculation. The results are shown in Table 2.

TABLE 2

| Sample No. | Time for stand (min) | | | |
| --- | --- | --- | --- | --- |
| | 0 | 30 | 60 | 120 |
| B | 100 | 0 | 0 | 0 |
| F | 100 | 0 | 0 | 0 |
| K | 100 | 0 | 0 | 0 |
| L | 100 | 100 | 80 | 25 |
| M | 100 | 100 | 100 | 95 |
| O | 100 | 0 | 0 | 0 |

As is also clear from Table 2 above, with samples other than samples L amd M, desired results can be obtained only when mixed with soil immediately after spreading. When samples other than samples L and M were allowed to stand after spreading, no substantial controlling effects were obtained. Contrary to this, in the case of samples L and M, even when the mixing thereof with soil was carried out after being allowed to stand for a relatively long time, the desired controlling effect could be obtained by sufficient diffusion of the active component from the test samples L and M.

EXAMPLE 3

A 40 part amount of powdered synthetic faujasite type zeolite having an effective pore diameter of about 4.2 Å (i.e., Molecular sieve 5A manufactured by UCC), 40 parts of diatomaceous earth, and 20 parts of bentonite were thoroughly mixed together in the presence of a sufficient amount of water in a mixer. Then, the mixture was extruded through a screw type extrusion granulator to form granules having a size of 1.6 mm diameter and about 3 mm length. The granules were fluidization dried at a temperature of 100° C. for 1 hour and, then, the dried granules were subjected to a thermal treatment at a temperature of about 450° C. under a vacuum pressure of 10 mmHg for 2 hours. Thus, a carrier sample was obtained.

The carrier thus obtained was supported with a solution of 1 part of MITC dissolved in 2 parts of 2,2'-dichloro-diisopropylether ("DCIP" hereinbelow) in the same manner as described in Example 1. Thus, the pesticide composition sample U was prepared.

The following pesticide composition samples V to Y (containing MITC/DCIP mixture) were prepared in the same manner as mentioned above, except that the following zeolites were used in lieu of Molecular sieve 5A.

| Sample | Zeolite |
| --- | --- |
| U | Molecular sieve 5A having an effective pore diameter of about 4.2 Å manufacture by UCC |
| V | Molecular sieve 4A having an effective pore diameter of about 3.5 Å manufactured by UCC |
| W | Molecular sieve 3A having an effective pore diameter of of about 2.5 Å manufactured by UCC |
| X | Molecular sieve 13X having an effective pore diameter of about 10 Å manufactured by UCC |
| Y | No zeolite was used. 80 parts of diatomaceous earth and 20 parts of bentonite were used. |

The samples U to Y were tested in the same manner as in Example 1. The resultant retention amounts of MITC and DCIP in the sample are shown in Tables 3 and 4, respectively.

TABLE 3

| Sample No. | MITC retention amount (%) | | | |
| --- | --- | --- | --- | --- |
| | Standing time (min) | | | |
| | 0 | 30 | 60 | 120 |
| U | 6.1 | 6.0 | 5.1 | 4.7 |
| V | 6.1 | 4.7 | 3.5 | 2.7 |
| W | 6.2 | 0.8 | 0 | 0 |
| X | 6.1 | 1.0 | 0 | 0 |
| Y | 6.2 | 0.7 | 0 | 0 |

TABLE 4

| Sample No. | DCIP retention amount (%) | | | |
| --- | --- | --- | --- | --- |
| | Standing time (min) | | | |
| | 0 | 30 | 60 | 120 |
| U | 13.4 | 10.2 | 7.5 | 2.9 |
| V | 13.5 | 10.1 | 7.4 | 3.0 |
| W | 13.2 | 10.3 | 7.2 | 3.1 |
| X | 13.3 | 10.1 | 7.0 | 2.8 |
| Y | 13.5 | 10.3 | 6.8 | 2.7 |

We claim:

1. A powdered or granular solid pesticide composition comprising 0.05 to 0.5 parts by weight of methyl isothiocyanate supported on 1 part by weight of natural or synthetic faujasite type zeolite particles having an effective micro-pore diameter of 3.5 to 4.2 angstroms.

2. A solid pesticide composition as claimed in claim 1, wherein said zeolite is type 4A or 5A synthetic zeolites.

3. A solid pesticide composition as claimed in claim 1, wherein said zeolite particles further contain an effective amount at least one additional pesticide supported thereon, said pesticide being selected from the group consisting of a nematocide, a soil fungicide and a soil insecticide.

4. A solid pesticide composition as claimed in claim 1, wherein the amount of the methyl isothiocyanate supported on the zeolite particles is 0.08 to 0.2 parts by weight based on 1 part by weight of the zeolite.

* * * * *